(12) United States Patent
Ogilvie et al.

(10) Patent No.: US 9,815,810 B1
(45) Date of Patent: Nov. 14, 2017

(54) METHOD OF CANNABINOID PRESERVATION THROUGH CRYSTALLIZATION AND OTHER CRYSTAL STRUCTURES

(71) Applicant: Deep Cell Industries Inc., Seattle, WA (US)

(72) Inventors: Kelly Ogilvie, Seattle, WA (US); Gary Bonilla, Seattle, WA (US)

(73) Assignee: DEEP CELL INDUSTRIES INC., Seattle, WA (US)

( * ) Notice: Subject to any disclaimer, the term of this patent is extended or adjusted under 35 U.S.C. 154(b) by 0 days.

(21) Appl. No.: 15/287,615

(22) Filed: Oct. 6, 2016

Related U.S. Application Data (60) Provisional application No. 62/309,459, filed on Mar. 17, 2016.

(51) Int. Cl.
| | | |
|---|---|---|
| *C07D 311/80* | (2006.01) | |
| *C07D 311/64* | (2006.01) | |
| *B01D 9/00* | (2006.01) | |
| *C07C 51/43* | (2006.01) | |

(52) U.S. Cl.
CPC .......... *C07D 311/80* (2013.01); *B01D 9/0009* (2013.01); *B01D 9/0031* (2013.01); *C07C 51/43* (2013.01); *C07D 311/64* (2013.01); *C07B 2200/13* (2013.01)

(58) Field of Classification Search
CPC .. C07D 311/80; C07D 311/64; B01D 9/0031; B01D 9/0009; C07C 51/43; C07B 2200/13
See application file for complete search history.

(56) References Cited

U.S. PATENT DOCUMENTS

2003/0229027 A1* 12/2003 Eissens ................ A61K 9/1652
514/23

\* cited by examiner

*Primary Examiner* — Matt Mauro
(74) *Attorney, Agent, or Firm* — FSP LLC (57) ABSTRACT

A method of cannabinoid preservation includes separating a cannabinoid ethanol (EtOH) mixture from a *cannabis* extract through a filtration process; forming a slurry by combining a crystalline compound with the cannabinoid EtOH mixture; heating and agitating the slurry in a pressurized chamber to form a colloidal cannabinoid EtOH mixture; distributing the colloidal cannabinoid EtOH mixture into a tray to form an evenly distributed mixture layer; forming an evaporation vessel for the evenly distributed mixture layer through the attachment of a detachable cover to the tray; positioning and heating the evaporation vessel within a heating chamber; performing a rapid cools process as the evenly distributed mixture layer approaches approaches saturation temperature; repeating the rapid cooling process until crystal formation is detected within the evenly distributed mixture layer; and/or removing the evaporation vessel from the heating chamber upon detection of crystal formation.

11 Claims, 8 Drawing Sheets

Cannabigerolic acid (CBG-A)

↓ CBDA Synthase

Cannabidiolic acid (CBDA)

CO2 ← ↓ Heat/Decarboxylation

Cannabidiol (CBD)

METHOD OF CANNABINOID PRESERVATION THROUGH CRYSTALLIZATION AND OTHER CRYSTAL STRUCTURES

CROSS-REFERENCE TO RELATED APPLICATIONS

This application claims priority to a provisional application filed on Mar. 16, 2016 with application No. 62/309,459.

BACKGROUND

Proper storage of *cannabis* products is known to preserve cannabinoids from oxidative degradation. Oxidative degradation of cannabinoids occurs due to an oxidative reduction reaction when a cannabinoid (reducant) is in the presence of an oxidizing agent (oxidant) such as oxygen. In the presence of oxygen, certain cannabinoids, such as isomers and some analogs of tetrahydrocannabinol, operate as electron donors for oxygen as their cyclic structure permits the formation of an aromatic ring following oxidation, forming the oxidized product cannabinol. Additional conditions may increase the rate of oxidation in cannabinoids such as humidity, high temperature and exposure to natural light or other sources of ultra violet (UV) light. Although the oxidative degradation of cannabinoids is expected, avoidance of favorable oxidative conditions may extend the shelf life of *cannabis* products.

Existing preservation methods may vary slightly depending on the cannabinoid products. For example, a traditional method of *cannabis* storage involves taking the flowers directly from the plant and submitting it through a drying process before storage. The drying process for flowers occurs at temperatures between 68° Fahrenheit (20° Celsius) for short periods of time in order to reduce humidity. The dried flowers are then placed in a sealed container at temperatures ranging between −4° Fahrenheit (−20° Celsius) for long term storage. Although this method preserves cannabinoids, it is a tedious and time consuming process with the end product taking up a noticeable amount of space.

Another method of storage is to combine extracted cannabinoids from flower and with oils for storage. Cannabinoids are soluble in certain oils allowing for the oil extracts to have a reduced storage volume. Unfortunately, these oil extracts require temperatures of approximately 39° Fahrenheit (4° Celsius) to maintain the solubility of cannabinoids in the oil extract. This temperature is problematic for long term storage as it is favorable for oxidative degradation. Although variations to this method exist by using different compounds such as lipophilic compounds of solid fats and phospholipids, alkaline phosphatases; in addition to monoglycosides such as malitol, lactitol and palatinit, these variations fail as an effective long term storage option for cannabinoids.

It is known that cannabinoids can be preserved by suspending the cannabinoid compounds in sugar and sugar alcohol glasses, which leads to improved bioavailability; nevertheless, problems persist wherein cannabinoids have been shown to degrade during the suspension process, and further degradation occurs during storage. This invention fills a long felt need for methods of preparing crystalline compositions that can be used to preserve cannabinoid compounds with increased storage capabilities and improved bioavailability.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

In the following description, various terms have the following meanings. Other terms have meanings as commonly understood in the relevant arts:

"reactor" in this context refers to a system or device to enable, induce, and/or facilitate the interaction between reactants leading to the formation of a product. A reactor may incorporate mechanical and/or electrical agents/structures as well as acoustic and light producing elements to facilitate product formation.

A method of cannabinoid preservation includes separating a cannabinoid ethanol (EtOH) mixture from a *cannabis* extract through a filtration process, forming a slurry by combining a crystalline compound with the cannabinoid EtOH mixture, and heating and agitating the slurry in a pressurized chamber to form a colloidal cannabinoid EtOH mixture.

The colloidal cannabinoid EtOH mixture is distributed into a tray to form an evenly distributed mixture layer. An evaporation vessel is formed for the evenly distributed mixture layer through the attachment of a detachable cover to the tray, and the evaporation vessel is positioned and heated within a heating chamber. A rapid cooling process is performed as the evenly distributed mixture layer approaches saturation temperature, and this process is repeated until crystal formation is detected within the evenly distributed mixture layer. The evaporation vessel is removed from the heating chamber upon detection of crystal formation.

In various embodiments, the cannabinoid EtOH mixture may include 0.05 to 2.5% cannabinoids by weight (wt) of the cannabinoid EtOH mixture. The slurry may be formed by combining the crystalline product with the cannabinoid EtOH mixture in a ratio ranging between 1:4 to 2.5:1 by weight of the cannabinoid EtOH mixture. The slurry may be heated and agitated in the pressurized chamber at a temperature ranging between 175° F. to 225° F. in a pressurized chamber between 45 and 75 minutes to form a colloidal cannabinoid EtOH mixture. The colloidal cannabinoid mixture may be distributed in the tray forming the evenly distributed mixture layer with a depth ranging between 2.0" and 4.0" inches, and the evaporation vessel may be heated in the heating chamber to a temperature ranging between 225° F. and 300° F.

The rapid cooling process may include temporarily removing the detachable cover from the tray to expose the evenly distributed mixture layer within the evaporation vessel, spraying pulverized dry ice on the evenly distributed mixture layer, and/or re-attaching the detachable cover to the tray.

The rapid cooling process may involve rapidly oscillating the temperature of the evenly distributed mixture layer in order to induce primary and secondary nucleation of the crystalline compound in the presence of the cannabinoids. The saturation temperature is the boiling point of a liquid and is the temperature for a corresponding saturation pressure at which a liquid boils into its vapor phase. The evaporation vessel may be coupled to a ventilation system to recover ethanol vapors while the evaporation vessel is heated within the heating chamber.

In some embodiments the crystalline compound may be a combination of at least two crystal forming compounds, where at least one of the crystal forming compounds may comprise antioxidants that include, but are not limited to, thiols of ascorbic acid.

Quantitative sampling results for the *cannabis* extract and the crystalline product to measure the performance of an embodiment of cannabinoid preservation are shown in Tables 1-4. Table 1 shows the cannabinoid profile of samples of the *cannabis* extract analyzed using Liquid Chromatography and Mass Spectroscopy (LCMS) analysis. Tables 2-4 show the cannabinoid profile of crystalline product samples analyzed using High-Performance Liquid Chromatography with Diode-Array Detection and Mass Spectrometry (HPLC-DAD-MS) analysis.

Variation in the analysis results may be due in part to the physical state and of the samples at standard temperature and pressure when the analysis was performed.

The cannabinoid profile may be set to detect cannabinoid precursors, isomers, and degradative products. The HLPC-DAD-MS analyzes crystalline products to determine the presence and quantity of Tetrahydrocannabinolic acid (THC-A), Cannabidiolic acid (cannabidiolate) (CBD-A), cannabigerolic acid (CBG-A), Δ-9-tetrahydrocannabivarinic Acid (THCV-A), Tetrahydrocannabinol-C4 (THC-C4-A), cannabicyclol acid (CBL-A), Δ-9-tetrahydrocannabinol (Δ9-THC), Cannabidiol (CBD), Cannabinol (CBN), Cannabichromene (CBC), Cannabigerol (CBG), Δ-8-tetrahydrocannabinol (Δ8-THC), Tetrahydrocannabivarin (THCV), and Cannabidivarin (CBDV). Tetrahydrocannabinolic acid (THC-A) is a biosynthetic precursor of tetrahydrocannabinol (THC) formed from enzymatic cyclization by of cannabigerloic acid by THCA synthase during the cyclization phase of the cannabinoid biosynthesis pathway. Cannabidiolic acid (CBD-A), also known as cannabidiolate, is a precursor of cannabindiol (CBD), formed during through enzymatic cyclization by CBDA synthase through stereo-specific oxidative cyclization of the geranyl group of cannabigerolic acid.

Cannabigerolic acid (CBG-A) is a product of prenylation of geranyl pyrophosphate and olivetolic acid. CBG-A is a precursor cannabinoid for Cannabigerol (CBC), Tetrahydrocannabinolic acid (THCA), Cannabidiolic acid (CBDA), and cannabichrome carboxylic acid (CBC-A) formed during the cyclization phase of the cannabinoid biosynthesis pathway. Δ-9-tetrahydrocannabivarinic acid (Δ-9-tetrahydrocannabinoloic acid, THCV-A) is a homolog of Δ-9-tetrahydrocannabinolic acid (THC-A) having a propyl side chain instead of a pentyl group. THCV-A is the cyclization product of cannabigerovarinic acid (CBGVA) by THCA synthase. CBGVA is the prenylation product of divarinolic acid, a homolog of olivetolic acid, and geranyl phosphate. THCV-A is also a precursor to Tetrahydrocannabivarin (THCV).

Tetrahydrocannabinolic acid C4 (Butyl-THC, THC-C4-A), is a homolog of Δ-9-tetrahydrocannabinolic acid and is differentiated by the replacement of a pentyl side chain with a butyl side chain. THC-C4 is rarely detected in significant quantities in plant samples. Cannabicyclol acid (CBL-A) is a degradative product of cannabichrome carboxylic acid (CBC-A) following UV absorption. Δ-9-tetrahydrocannabinol (Δ9-THC) is the degradative product of Δ-9-tetrahydracannibinoloic acid (THCA) from decarboxylation following exposure to heat and/or air and is the principal psychoactive constituent of *cannabis*.

Cannabidiol (CBD) the degradative product of Cannabidiolic acid due to decarboxylation following exposure to heat and/or air. CBD is a major phytocannabinoid, accounting for up to 40% of *cannabis* plant's extract. Cannabinol (CBN) is the degradative product of Δ9-tetrahydrocannabinol (Δ9-THC) and its isomer Δ-8-tetrahydrocannabinol (Δ8THC) due to oxidative degradation following exposure to oxygen and heat. Incidentally, higher levels of CBN may be an indicator of age and/or improper storage of a sample.

Cannabichromene (CBC) degradative product of cannabichrome carboxylic acid CBC-A (CBG-A) following decarboxylation due to exposure to heat or UV light. Cannabigerol (CBG) is the degradative product of cannabigerloic acid (CBG-A) following decarboxylation following exposure to heat and oxygen. Δ-8-tetrahydrocannabinol (Δ8-THC) is an isomer of Δ-9-tetrahydrocannabinol that is rarely produced in significant amounts in *cannabis* plants.

Tetrahydrocannabivarin (THCV), is a homolog of Δ9-tetrahydrocannabinol with a propyl side chain replacing the pentyl side chain, and the degradative product of tetrahydrocannabivarinic Acid (THCV-A) following decarboxylation due to exposure to heat or UV light. Cannabidivarin (CBDV) is a homolog of Cannabidiol (CBD), with a propyl side chain replacing the pentyl side-chain. CBDV is the decarboxylation product of Cannabidivarinic Acid (CBDV-A). CBDV-A is cyclization product of CBGVA by CBDVA synthase. CBGVA is the prenylation product of divarinolic acid, a homolog of olivetolic acid, and geranyl phosphate.

TABLE 1

| Cannabinoids | Sample RB Fat mg/ml |
| --- | --- |
| THC-A | 37.07 |
| CBD-A | 0.12 |
| CBG-A | 1.22 |
| THCV-A | 0.26 |
| THC-C4-A | — |
| CBL-A | 0.38 |
| Δ9-THC | 12.85 |
| CBD | — |
| CBN | 0.3 |
| CBC | 0.63 |
| CBG | 0.69 |
| Δ8-THC | — |
| THCV | — |
| CBDV | — |

Table 1 shows a cannabinoid profile for a sample of the *cannabis* extract generated using LCMS analysis. LCMS analysis quantifies the presence of cannabinoids in the cannabis extract as mg/ml. The cannabis extract is utilized in subsequent analyses of the crystalline product produced through the method of cannabinoid preservation. The analyzed cannabis extract is labeled as "RB Fat". The cannabinoid profile for RB Fat, shows lower concentrations of cannabinoids formed through decarboxylation and photooxidative reactions (CBD, CBN, CBC, CBG, Δ9-THC, Δ8-THC, THCV, and CBDV) relative to their precursors (THC-A, CBD-A, CBG-A, and THCV-A).

TABLE 2

| Cannabinoids | Sample R103A mg/g | Sample R103B mg/g | Sample R103C mg/g | Avg R103A-C mg/g |
|---|---|---|---|---|
| THC-A | 7.13 | 6.18 | 3.08 | 5.46 |
| CBD-A | — | — | — | — |
| CBG-A | — | — | — | — |
| THCV-A | 0.05 | — | — | 0.02 |
| THC-C4-A | — | — | — | — |
| CBL-A | 0.46 | 0.35 | 0.35 | 0.39 |
| Δ9-THC | 15.56 | 16.18 | 15.64 | 15.79 |
| CBD | — | — | — | — |
| CBN | 0.93 | 1 | 1.16 | 1.03 |
| CBC | 0.47 | 0.45 | 0.42 | 0.45 |
| CBG | 0.32 | 0.26 | 0.26 | 0.28 |
| Δ8-THC | — | — | 0.18 | 0.06 |
| THCV | 0.14 | 0.2 | 0.15 | 0.16 |
| CBDV | — | — | — | — |

Table 2 shows a cannabinoid profile for samples of the crystalline product labeled R103A-C generated using HPLC-DAD-MS analysis. Samples R103A-C are crystalline products generated through the method of cannabis preservation without the rapid cooling process and using the cannabis extract labeled "RB Fat" that use sucrose as the crystalline compound. Samples R103A-C show relative consistency with regards to quantity and presence of cannabinoids in the cannabinoid profile with the exception of THCV-A in Sample R103A and Δ8-THC in Sample R103C. An average of the sample values was calculated and labeled as Avg R103A-C. The sample averages show higher quantities of decarboxylated cannabinoids relative to their precursors. The sample average shows lower quantities of THC-A relative to quantities of its degradative product Δ9-THC. Although no quantity of CBG-A was detected, its degradative product CBG was detected at an average quantity of 0.28 mg/g suggesting a high degree of degradation. Similarly, THCV-A shows low detected quantities relative to its degradative product THCV which is found at an average quantity of 0.16 suggesting a high degree of degradation. No detectable quantities of the CBD-A or its degradative product CBD were detected. A % RSD was calculated for all non-zeroed cannabinoid sample sets (38.8% RSD for THC-A, 16.4% RSD for CBL-A, 2.1% RSD for Δ9THC, 11.4% RSD for CBN, 5.6% RSD for CBC, 12.4% RSD for CBG, and 19.7% RSD for THCV) and shows deviation below 20% for cannabinoids with the exception of THC-A.

TABLE 3

| Cannabinoids | Control R104 mg/g | Sample R104A mg/g | (Retest) Sample R104A mg/g | Sample R104B mg/g |
|---|---|---|---|---|
| THC-A | 0.02 | 0.03 | — | — |
| CBD-A | — | — | — | — |
| CBG-A | — | — | — | — |
| THCV-A | — | — | — | — |
| THC-C4-A | — | — | — | — |
| CBL-A | — | — | — | — |
| Δ9-THC | 35.37 | 57.13 | 57.45 | 60.42 |
| CBD | 0.17 | 0.08 | 0.15 | 0.17 |
| CBN | 0.57 | 1.17 | 1.26 | 1.28 |
| CBC | 0.8 | 1.18 | 1.15 | 1.22 |
| CBG | 0.82 | 1.34 | 1.29 | 1.25 |
| Δ8-THC | 1.7 | — | 1.36 | 0.14 |
| THCV | 0.34 | 0.54 | 0.52 | 0.55 |
| CBDV | — | — | — | — |

Table 3 shows a cannabinoid profile of samples of the crystalline product labeled R104A-B generated using HPLC-DAD-MS analysis. Samples R104A-B are crystalline products generated through the process of cannabinoid preservation that includes the rapid cooling process using sucrose as the crystalline compound. In order to provide an accurate baseline measurement to compare the effectiveness of the rapid cooling process, a control sample was generated using the method of cannabindoid production without the rapid cooling process. The control sample is labeled Control R104 shows undetectable quantities for the cannabinoid precursor (THC-A, CBD-A, CBG-A, and THCV-A) relative to decarboxylation and photooxidative reaction products (CBD, CBN, CBC, CBG, Δ9-THC, Δ8-THC, THCV, and CBDV). With the exception of Δ9-THC and Δ8-THC, the degradation product cannabinoids are found in quantities that do not exceed 1 mg/g of the sample. Sample R104A is a sample generated through the cannabinoid preservation process that has undergone the rapid cooling process. Sample 104A shows negligible or no detectable quantities of cannabinoid precursors THC-A, CBD-A, CBG-A, and THCV-A). In Sample R104A, the Δ9-THC quantities show a 62% increase at 57.13 mg/g compared to the 35.37 mg/g in the control sample. For comparison the other degradative cannabinoids of Sample R104A show similar increases CBN 1.17 mg/g vs control 0.57 mg/g; CBC 1.18 mg/g vs control 0.8 mg/g; CBG 1.34 mg/g vs control 0.82 mg/g; and THCV 0.54 mg/g vs control 0.34 mg/g). The exception to the increase is CBD 0.08 mg/g vs control 0.17 mg/g, which showed a decrease in quantity and the Δ8-THC which showed no detectable quantities compared to the control. Sample R104A was retested and showed similar results to the original sample results with the exception of the CBD having a smaller relative reduction compared to the original test while showing detectable quantities for Δ8-THC. Sample R104B is a sample generated through the cannabinoid crystallization process that underwent the rapid cooling process. Unlike Sample R104A, Sample R104B was stored for three months before being tested to quantify the degradation of the cannabinoids while the crystalline product was in storage. Sample R104B minimal increases in CBN 1.28 mg/g when compared to Sample R104A 1.17 mg/g and Sample R104A Retest 1.26 mg/g. CBN is indicators of oxidative degradation of Δ9-THC and Δ8-THC. In Sample R104B a decrease in Δ8-THC 0.14 mg/g was seen relative to Sample R104A Retest 1.36 mg/g. However, Δ9-THC in R104B showed an increase relative to Sample R104A (original and Restest) at 60.42 mg/g vs 57.13 mg/g and 57.45 mg/g respectively. The increase of Δ9-THC may be indicative of isomerization of Δ8-THC returning to a more stable configuration of Δ9-THC.

TABLE 4

| Cannabinoids | Sample S103 mg/g | Sample S201 mg/g |
| --- | --- | --- |
| THC-A | — | — |
| CBD-A | — | — |
| CBG-A | — | — |
| THCV-A | — | — |
| THC-C4-A | — | — |
| CBL-A | — | — |
| Δ9-THC | 21.92 | 40.04 |
| CBD | 0.22 | 0.11 |
| CBN | 2.33 | 0.79 |
| CBC | 0.94 | 0.84 |
| CBG | 0.58 | 0.93 |
| Δ8-THC | — | — |
| THCV | 0.51 | 0.41 |
| CBDV | — | — |

Table 4 shows a cannabinoid profile of a crystalline product generated through the process of cannabinoid preservation with and without the inclusion of the rapid cooling process, and with the crystalline compound being a salt, specifically sodium chloride. The values for the Samples S103 and Samples S201 where generated using HPLC-DAD-MS analysis. Sample S103 is the sample generated through the cannabinoid preservation process without the rapid cooling process using the Cannabinoids sourced RB-Fat. Sample S201 is the sample generated through the cannabinoid preservation process with the rapid cooling process. Sample S201 shows a two-fold increase in the Δ9-THC when compared to the Sample S103 (S201 40.04 mg/g vs S103 21.93 mg/g). Which is similar to the results observed in Samples R103A-B. However, Sample S201 showed a significant reduction in CBN vs the Sample S103 (S201 0.79 mg/g vs S103 2.33 mg/g). The other degradation products (CBD, CBC, CBG, and THCV) of S201 showed marginal differences in cannabinoid quantity relative to the S103.

The disclosed processes for cannabinoid preservation may be utilized to infuse sugar, salt, sugar-alcohol, and/or other crystalline compounds with cannabinoids. The cannabinoid may be phytocannabinoid derived from a *Cannabis sativa* L. variety, but may be any cannabinoid, including any endocannabinoid or any synthetic cannabinoid. The processes may be utilized to infuse cannabinoids in sugars such as glucose, fructose, and sucrose, as well as salt and sugar alcohol crystals. The crystalline products formed thereby may reduce the degradation of cannabinoids during long-term storage and increase bioavailability.

The disclosed processes may be utilized to stabilize, fuse, and preserve cannabinoids using sugars, salts, sugar alcohols, and any other crystalline compound through the utilization of heat, pressure, and rapid temperature oscillation to facilitate and induce crystallization in the cannabinoid preservation process.

One embodiment may include the use of *cannabis* extracts from a supercritical and subcritical carbon dioxide extraction, hydrocarbon extraction, or water extraction in combination with the alcohol extraction and a membrane filtration process to separate a cannabinoid ethanol mixture. The processes may utilize glucose, fructose, sucrose, sodium chloride, and xylitol as the crystalline compound to create a crystalline structure in combination with the use of alcohol and membrane filters. The filtration process may combine cannabinoid extract with an alcohol at 200° Fahrenheit (93° Celsius), to aid in dissolution, followed by vigorous agitation.

The filtration process may lower the temperature of the *cannabis* extract and ethanol mixture to a temperature below 0° Fahrenheit (−18° Celsius) for 24 hours in order to crystallize lipids from the *cannabis* extract and ethanol mixture. Subsequently, crystallization of lipids facilitates removal through membrane filtration.

A slurry may be formed by blending and agitating the ethanol cannabinoid mixture with the crystalline compound by placing the slurry into a pressure chamber and heated to 200° Fahrenheit (93° Celsius) for sixty minutes. An additional crystalline compound may be added to the slurry to seed crystal formation and the mixture may be heated to 220° Fahrenheit (104° Celsius) for another sixty minutes and the crystal size of the product is homogenized during a polishing step.

The crystalline product may be a nearly pure cannabinoid infused crystal, which may be a sugar, salt or sugar-alcohol crystal that is useful for preserving cannabinoids against degradation in a biologically available and ecologically safe crystalline formulation. The preservation process may preserve terpenophenolic compounds by fusing the extracted terpenophenolic compounds into salt, sugar, and sugar alcohol crystals. The lattice structure and optical characteristics of the infused crystal assists in the preservation and stability of the terpenophenolic compound for long-term storage and use in medicaments.

The term fusing refers to the process of suspending terpenophenolic compounds in crystalline salt, sugar and sugar alcohol structures by using the methods disclosed. The method of cannabinoid preservation prevents the terpenophenolic compounds from being damaged by exposure to light, oxygen, chlorophylls, and free radicals, all of which are known to degrade cannabinoids.

The crystal bond orientation prevents chemical, photo-oxidation and further decarboxylation of the terpenophenolic compounds. The method of cannabinoid preservation is suitable for other forms of molecular stabilization. the method utilizes membrane filtration to aid in stability and solubility, as well as the use of temperature oscillation to change the chemical nature of the crystalline product. The terpenophenolic compound may be a cannabinoid, a terpenoid, a flavonoid, or any other compound or combination thereof.

In some embodiments, the cannabinoids are fused into the crystal lattices of a sugar, salt, sugar alcohol and/or other crystalline compound and applicable combinations thereof. In some embodiments, the lattice structure of the crystalline compound may be manipulated through external forces, (pressure, temperature, chemical, etc.) to modify the lattice structure and formation. The process may result in a terpenophenolic compound preserved in the lattice of sugar, xylitol, and salt crystals.

Principles of green chemistry may be implemented to provide safe alternatives to industrial pharmaceutical manufacturing processes. The preserved cannabinoid may experience improved uptake and absorption as well as sustained bioavailability through imparted by the digestion and absorption patterns associated with consumption of unaltered crystalline compound. In addition, the preserved cannabinoid within the crystalline product may be well suited for use in edible medicaments as a result of the hydrolysis of the disaccharides into fructose and glucose. The process may improve the absorption of cannabinoids, terpenes, and other terpenophenolic compounds during digestion, without decreased bioavailability from excessive absorption into the stomach and liver tissues. The process may provide improved water solubility, which aids in its use as a medicament.

In one embodiment, the potency of the *cannabis* infused crystals is 2 mg/g to 17 mg/gram as the crystallization may prevent losses in concentration or potency degradation from the *cannabis* extract.

A cannabinoid infused crystalline product that results from application of the disclosed preservation processes prevents oxidation, decarboxylation, and degradation to the cannabinoids, which are bound to non-lipid molecules aiding use in preservation and consumption. The crystalline product of the method of cannabinoid preservation exhibits unique chemical properties comprising resistance to heat, light, spoilage, and excessive metabolic absorption in the body when consumed.

The process may carry beneficial improvements in absorption rates, as the lipid-based cannabinoid compositions require a complex digestion pathway, where as the crystalline product of the method of cannabinoid preservation may adopt the digestion pathway and absorption profile of the crystalline compound.

The process may be modified for application in a manufacturing process. The manufacturing process may begin with the extraction of terpenophenolic/cannabinoid compounds, preferable cannabinoids, from a plant, preferably *Cannabis sativa* L., using supercritical carbon dioxide extraction. In an alternate configuration, the terpenophenolic/cannabinoid compounds are extracted using a subcritical carbon dioxide extraction, or hydrocarbon extraction, or water extraction, and/or any combination of these extraction processes known to extract the target terpenophenolic compounds. In either configuration, the extraction may be carried out in a reactor controlled autonomously or under human supervision.

The manufacturing process may then proceed to an alcohol extraction phase by mixing and agitating the *cannabis* extract in an alcohol that is raised to a temperate of 200° Fahrenheit (93° Celsius). In an embodiment, 95.5% ethanol is selected for the extraction but the alcohol may be any alcohol effective as a solvent for *cannabis* extraction.

Ethanol is selected as the alcohol solvent due to its solvation properties and low toxicity to humans. The ratio of alcohol to *cannabis* extract may be 4:1 to 8:1, but may be 5:1, 6:1, or 7:1. A ratio between 4:1 and 8:1 allows a full blending as well as control over the final concentration of the cannabinoids in the crystal matrix.

In an embodiment, the temperature of the extract-alcohol mixture may be raised to 200° Fahrenheit (93° Celsius) during agitation and mixing, in order to release terpenophenolic/cannabinoid compounds from the extract. The selected temperature of 200° Fahrenheit (93° Celsius) is selected based on the boiling point of ethanol at 173° Fahrenheit (78° Celsius) and the boiling point of THC at 315° Fahrenheit (157° Celsius), and the boiling point of Cannabidiol (CBD) at 356° Fahrenheit 180° Celsius. 200° Fahrenheit (93° Celsius) offers an intermediate point for well suited for blending, as the temperature is above ethanol's boiling point and below the boiling point of the cannabinoids. The surface tension and fluid dynamics allow good mixing conditions as a result of the phase transition of ethanol from liquid to vapor. The ethanol extraction may be carried out in a reactor or reaction vessel and may additionally incorporate the use of an agitator to agitate extract-alcohol mixtures is used.

The method of cannabinoid preservation may utilize a mixer that has a mechanical agitation speed of at least 20,000 rpm. Additional agitations speeds and ranges may be utilized to accommodate variations and improvements to the manufacturing process. The blended mixture of cannabinoids and alcohols may be above 150° Fahrenheit (66° Celsius) for handling, mixing and homogenization.

The alcohol extraction phase may be followed by a cooling process to bring the mixture to a temperature below 0° Fahrenheit (−18° Celsius) for a period of 24 hours or greater in order to induce nucleation and formation crystallized lipid structures. The temperature change may occur rapidly over a short time period in order to cause rapid primary and secondary nucleation to form lipid crystals. In an alternate configuration, the temperature change may occur gradually over an extended period of time in order to induce homogenous nucleation for lipid crystallization. The cooling of fats to below their melting point leads to crystallization of the fat compounds. The crystallization is divided into nucleation and crystal growth. During cooling, the crystalline nucleus forms and begins to grow by incorporating other molecules over a time period of 24 hours or more. In an embodiment, the time and temperature of the freezing process have a direct correlation to the solidification of the lipids; therefore, a cold and short period of time.

The cooling of the *cannabis* extract may be followed by a filtration process. The cooling of the *cannabis* extract forms a cooled suspension that includes cannabinoids and crystallized lipids in EtOH. The cooled suspension is passed through a thirty micron-membrane filter in order to exclude lipid crystals that are larger than thirty microns as part of the filtration process. The remaining filtrate is a colloidal mixture of cannabinoids and lipid crystals smaller than 30 microns in EtOH. In an embodiment, the mixture is passed through a second, twenty micron-membrane filter, to exclude lipid crystals larger than twenty microns. In an alternate embodiment, the mixture is passed through a ten micron-membrane filter to exclude lipid crystals larger than ten microns. In another embodiment, all three membrane filters are used to separate the crystallized lips in the cooled cannabinoid extracts. In other embodiments, the membrane filtration process may be repeated as necessary. The method of cannabinoid preservation utilizes filters of specific size to selectively and concurrently exclude longer chain fats, waxes, and other compounds which hinder the process of crystallization.

The filtration process may be accomplished using an electromagnetic filtration process that allows separation of lipid from the cannabinoid products. A crystalline compound such as but no limited to a micronized sugar, salt or sugar alcohol may be added to the filtered cannabinoid-ethanol mixture. In an embodiment, the crystalline compound may be accomplished by sucrose but may be substituted for glucose, fructose, or sucralose. The micronized sugar may be accomplished by a micronized sugar alcohol, such as xylitol. Additionally, Glycerol may be selected for its non-toxic sweetening and preservation properties. The crystalline compound may be accomplished by a micronized salt is added to cannabinoid-ethanol mixture. The micronized salt may be accomplished with sodium chloride, or any other salt that is suitable for consumption.

The crystalline compound and alcohol cannabinoid mixture may be agitated and blended into a slurry. The slurry may be combined in a reactor comprising a mixer/agitator that has a minimum agitation speed of 20,000 rpm. The slurry may be agitated for a period of time that exceeds five minutes. The slurry may be heated to 200° Fahrenheit (93° Celsius) in a pressure chamber for sixty minutes or a period of time adapted to accommodate improvements or modifications to the manufacturing process. The pressure chamber is heated to a temperature range of 200° to 250° Fahrenheit (93 to 121° Celsius) at normal atmospheric pressure. At higher pressures ranging from two atmospheres (202 kpa) the temperature range is between 250° to 300° Fahrenheit (121 to 148° Celsius).

The slurry may be transferred to a tray and spread evenly to form an evenly distributed layer. The evenly distributed layer material may be provided with a depth ranging between 25-50% of the height of the tray. The depth of the distributed layer is dependent on exposed surface area of the evenly distributed layer to facilitate vaporization of excess ethanol. The tray is coupled to a detachable cover that partially seals evenly distributed layer forming an evaporation vessel. The evaporation vessel serves as a partially sealed enclosure that impedes rapid vaporization of alcohol under heat while reducing factors that could lead to the auto ignition of the alcohol vapors.

The evaporation vessel may be placed within a heating chamber and monitored for the saturation temperature/boiling point of the evenly distributed layer. Upon detection that the evenly distributed layer is approaching the saturation temperature/boiling point, the detachable cover of the evaporation vessel is removed and the evenly distributed layer is sprayed with pulverized dry ice as part of a rapid cooling process. The evenly distributed layer is inspected to determine nucleation or crystal growth before the detachable cover is reattached to the tray. During the rapid cooling process, the evaporation vessel remains within the heating chamber. The rapid cooling process is repeated until crystal growth is detected or all the alcohol has been boiled off.

The pulverized dry ice ($CO_2$) may be substituted with another super cooled substance that may include but is not limited to liquid nitrogen. Dry ice may be selected preferentially based on its sublimation properties. The sublimation of dry ice in an alcohol containing fluid increases vaporization by allowing the saturation pressure to be reached below the normal saturation temperature. Removal of alcohol through dry ice simultaneously lowering the temperature of the cannabinoids. The evaporation vessel may be removed from the heating chamber following detection of crystal growth in the evenly distributed layer following application of the rapid cooling process.

The preservation process may include a further step wherein the micronized material is added to the colloidal alcohol-cannabinoid mixture at the midway point of the process and at peak temperature. The micronized material seeds crystal formation as alcohol evaporates from the slurry and the cannabinoid crystals nucleate.

The preservation process may further include additional crystalline compound to the slurry to seed the crystal formation. In the aforementioned embodiment, the crystalline compound may be a micronized material that is preferably sugar, salt or a sugar alcohol, but in additional embodiments be accomplished by the use of xylitol or glycerol. In alternate embodiments, the crystalline compound is a salt, preferably sodium chloride.

A system for preserving cannabinoids in a crystalline product may include a first reactor, a filtration process, a second reactor, a pressurized chamber, an evaporation vessel, a heating chamber, the first reactor, the first reactor, the filtration process, the second reactor, the pressurized chamber, the tray, the evenly distributed mixture layer, the evaporation vessel, and/or the evenly distributed mixture layer.

The evaporation vessel may include a detachable cover detachably coupled to a tray.

In some embodiments, the first reactor may be operatively disposed to receive *cannabis* material and ethanol.

In some embodiments, the first reactor may be in fluid communication with the filtration process to deliver a *cannabis* extract.

In some embodiments, the filtration process may be in fluid communication with the second reactor for delivery of a cannabinoid ethanol (EtOH) mixture separated from the *cannabis* extract.

In some embodiments, the second reactor may be operatively disposed to receive a crystalline compound.

In some embodiments, the pressurized chamber may be operatively disposed to receive a slurry from the second reactor.

In some embodiments, the tray may be in operatively disposed to receive a colloidal cannabinoid EtOH mixture from the pressurized chamber forming an evenly distributed mixture layer.

In some embodiments, the evenly distributed mixture layer may be enclosably positioned within the evaporation vessel.

In some embodiments, the evaporation vessel may be positionable within the heating chamber.

In some embodiments, the evenly distributed mixture layer may be in fluid communication with pulverized dry ice following detachment of the detachable cover from the tray.

Figure 1:
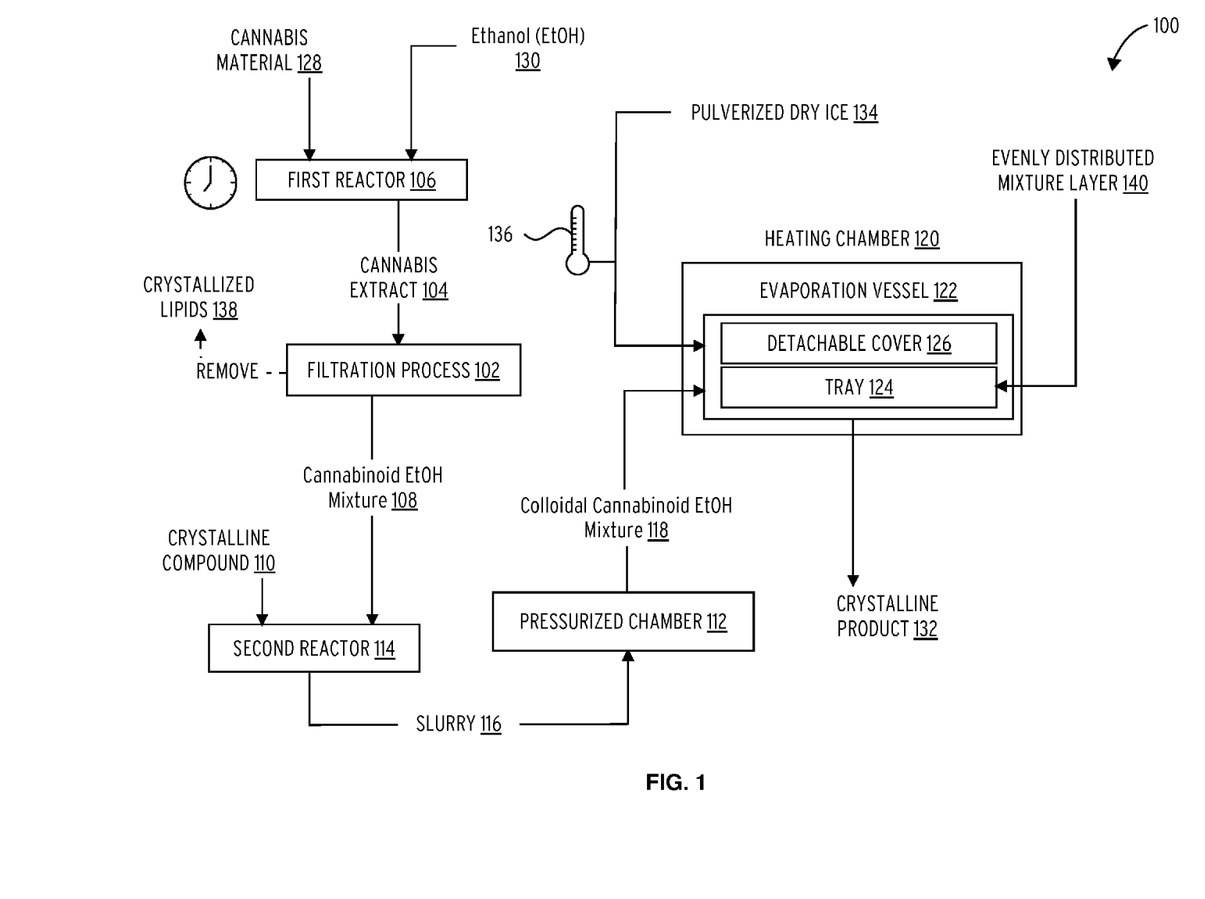
FIG. 1 illustrates an embodiment of a system for preserving cannabinoids in a crystalline product 100.
Figure 2:
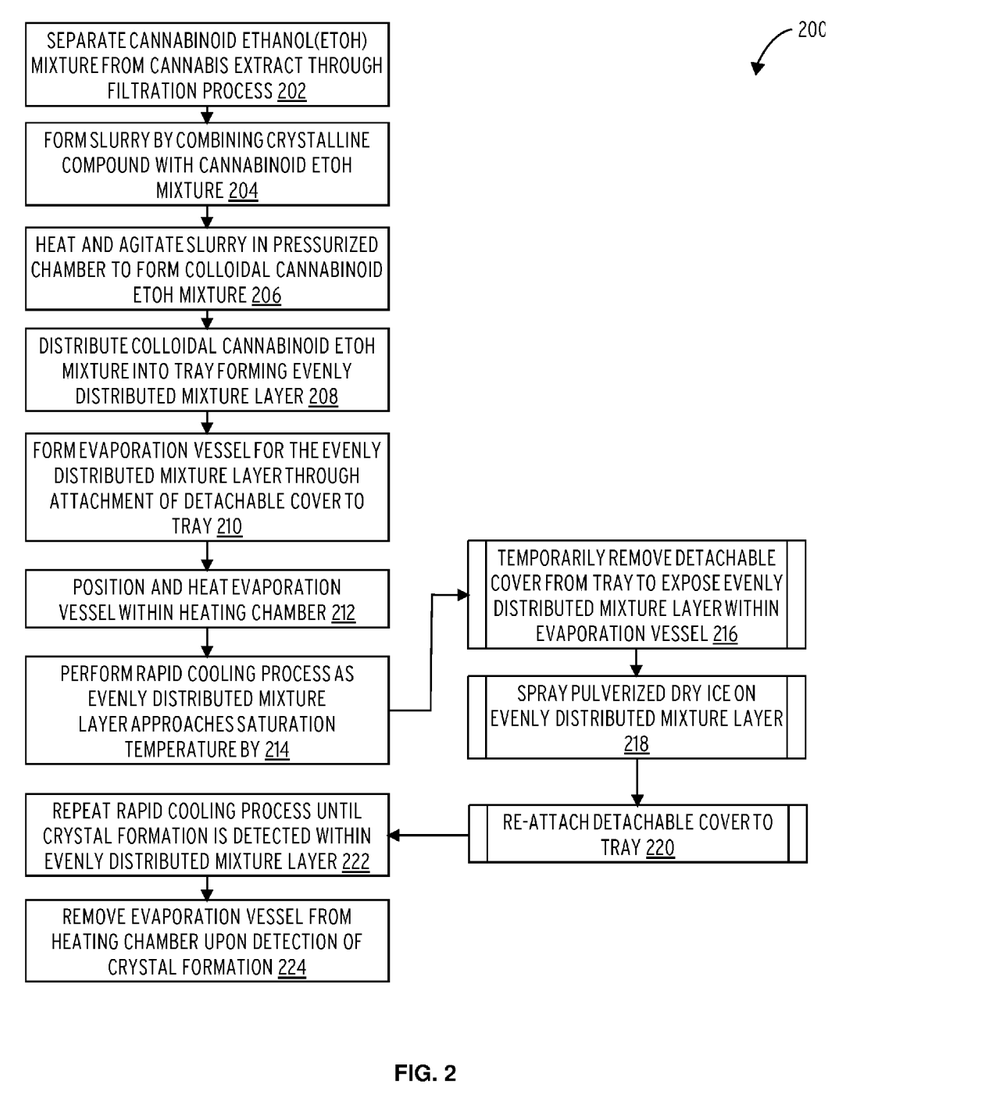
FIG. 2 illustrates an embodiment of a process of preserving cannabinoids in a crystalline product 200.

FIG. 2 illustrates an embodiment of a system for preserving cannabinoids in a crystalline product 100. The system for preserving cannabinoids in a crystalline product 100 comprises a first reactor 106, a filtration process 102, a second reactor 114, a pressurized chamber 112, and a heating chamber 120. The first reactor 106 combines *cannabis* material 128 and ethanol (EtOH) 130 to form a *cannabis* extract 104. The filtration process 102 removes crystallized lipids 138 from the *cannabis* extract 104 leaving a cannabinoid EtOH mixture 108. The second reactor 114 combines the cannabinoid EtOH mixture 108 and a crystalline compound 110 to form a slurry 116. The pressurized chamber 112 forms a colloidal cannabinoid EtOH mixture 118 from the slurry 116. The heating chamber 120 comprises an evaporation vessel 122. The evaporation vessel 122 comprises a detachable cover 126 detachably couple to a tray 124. The tray 124 comprises an evenly distributed mixture layer 140. When the evenly distributed mixture layer 140 within the evaporation vessel 122 approaches the saturation temperature 136, pulverized dry ice 134 is sprayed as part of a rapid cooling process. The evaporation vessel 122 is removed from the heating chamber 120 upon detection of crystal formation indicating production of a crystalline product 132. The process of preserving cannabinoids in a crystalline product 200 may be operated in accordance with the process described in FIG. 2.

Referencing FIG. 2, a process of preserving cannabinoids in a crystalline product 200 separates a cannabinoid ethanol (EtOH) mixture from a *cannabis* extract through a filtration process (block 202). A slurry is formed by combining a crystalline compound with the cannabinoid EtOH mixture (block 204). A colloidal cannabinoid EtOH mixture is formed from heating and agitating the slurry in a pressurized chamber (block 206). An evenly distributed mixture layer is formed by distributing the colloidal cannabinoid EtOH mixture into a tray (block 208). An evaporation vessel is formed enclosing the evenly distributed mixture layer by the attachment of the detachable cover to the tray (block 210). The evaporation vessel is positioned and heated within a heating chamber (block 212). A rapid cooling process is performed as the evenly distributed mixture layer approaches a saturation temperature (block 214). The rapid cooling process includes the temporary removal of the detachable cover from the tray to expose the evenly distributed mixture layer within the evaporation vessel (subroutine block 216), spraying pulverized dry ice on the evenly distributed mixture layer (subroutine block 218), and re-attaching the detachable cover to the tray (subroutine block 220). The rapid cooling process is repeated each instance the evenly distributed mixture layer approaches the saturation temperature, until the crystal formation is detected within the evenly distributed mixture layer (block 222). The evaporation vessel is removed from the heating chamber upon detection of the crystal formation (block 224).

Figure 3:
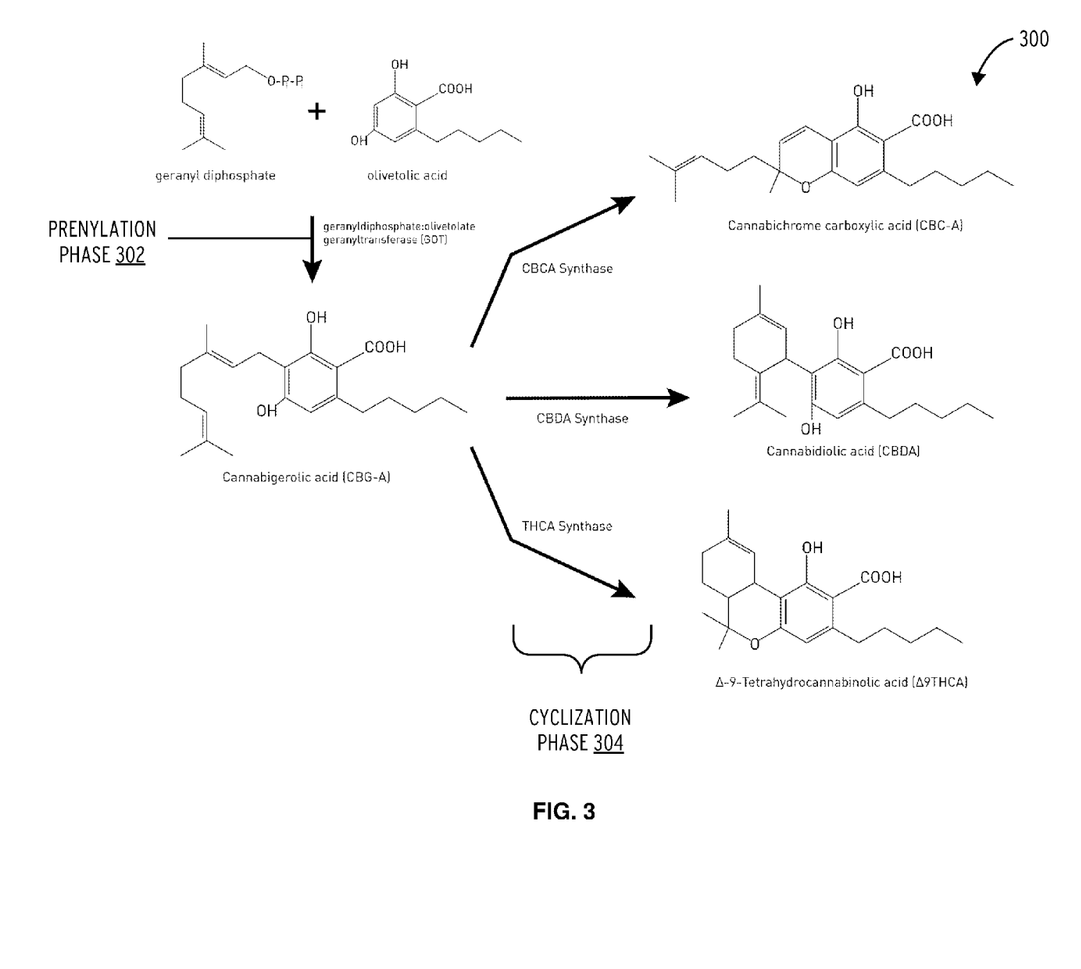
FIG. 3 illustrates biosynthesis process 300 for forming cannabigerolic acid and derived cannabinoid reaction products.

Referencing FIG. 3, the biosynthesis process 300 illustrates the formation of cannabigerolic acid (CBG-A) from the geranyl diphosphate and olivetolic acid as part of a prenylation phase 302. Cannabigerolic acid is a cannabinoid precursor for the formation of Cannabigerol (CBG), cannabichrome carboxylic acid (CBC-A), Cannabidiolic acid (CBD-A), and Δ-9-tetrahydrocannabinolic acid (Δ9-THCA/THCA). Cannabichrome carboxylic acid, Cannabidiolic acid, and Δ-9-tetrahydrocannabinolic acid are formed from cannabigerolic acid following cyclization phase 304 by CBCA synthase, CBDA synthase, and THCA synthase enzymes, respectively. Cannabigerol is the degraditive product of cannabigerolic acid as a result of decarboxylation due to exposure to heat.

Figure 4:
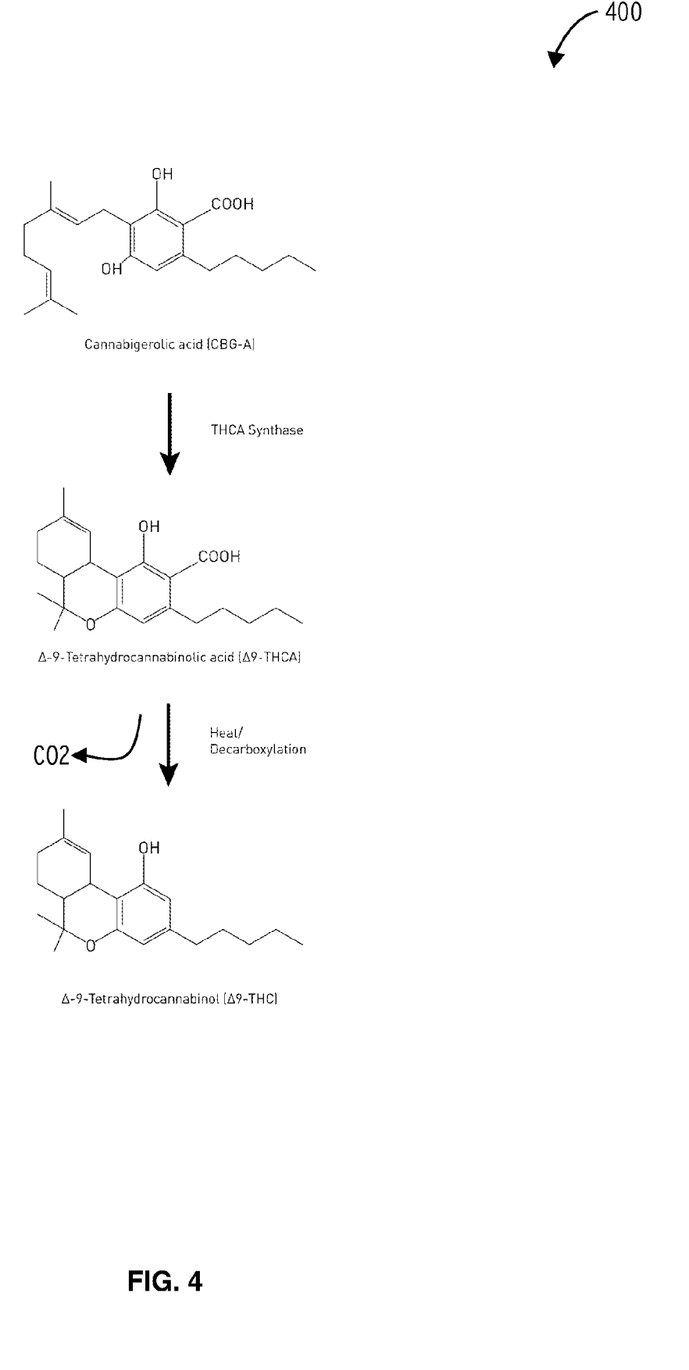
FIG. 4 illustrates biosynthesis pathway 400 showing the production of Δ-9-tetrahydrocannabinol.

Referencing FIG. 4, biosynthesis pathway 400 illustrates the production of the Δ-9-tetrahydrocannabinol from cannabigerolic acid. The biosynthesis pathway 400 begins after the prenylation phase with cannabigerolic acid. Δ-9-tetrahydrocannabinolic acid is formed following stereospecific oxidative cyclization of cannabigerolic acid by tetrahydrocannabinolic acid synthase during the cyclization phase. Δ-9-tetrahydrocannabinolic acid undergoes decarboxylation when exposed to heat or releasing $CO_2$ and forming the degradative product Δ-9-tetrahydrocannabinol.

Figure 5:
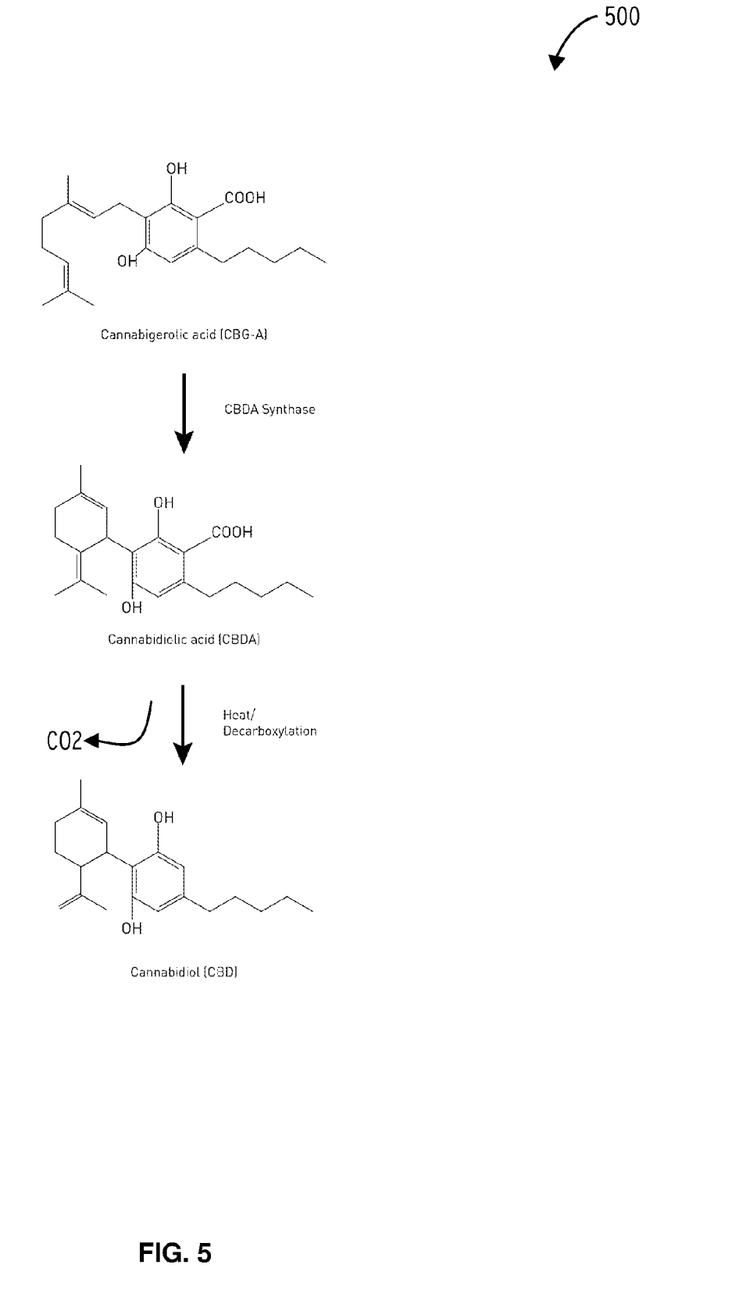
FIG. 5 illustrates biosynthesis pathway 500 showing the production of Cannabidiol.

Referencing FIG. 5, biosynthesis pathway 500 illustrates production Cannabidiol from the cannabigerolic acid. The biosynthesis pathway 500 begins after the prenylation phase with cannabigerolic acid. Cannabidiolic acid (CBDA) is formed following stereospecific oxidative cyclization of cannabigerolic acid by CBDA synthase during the cyclization phase. Cannabidiolic acid undergoes decarboxylation when exposed to heat releasing $CO_2$ and forming the degradative product Cannabidiol.

Figure 6:
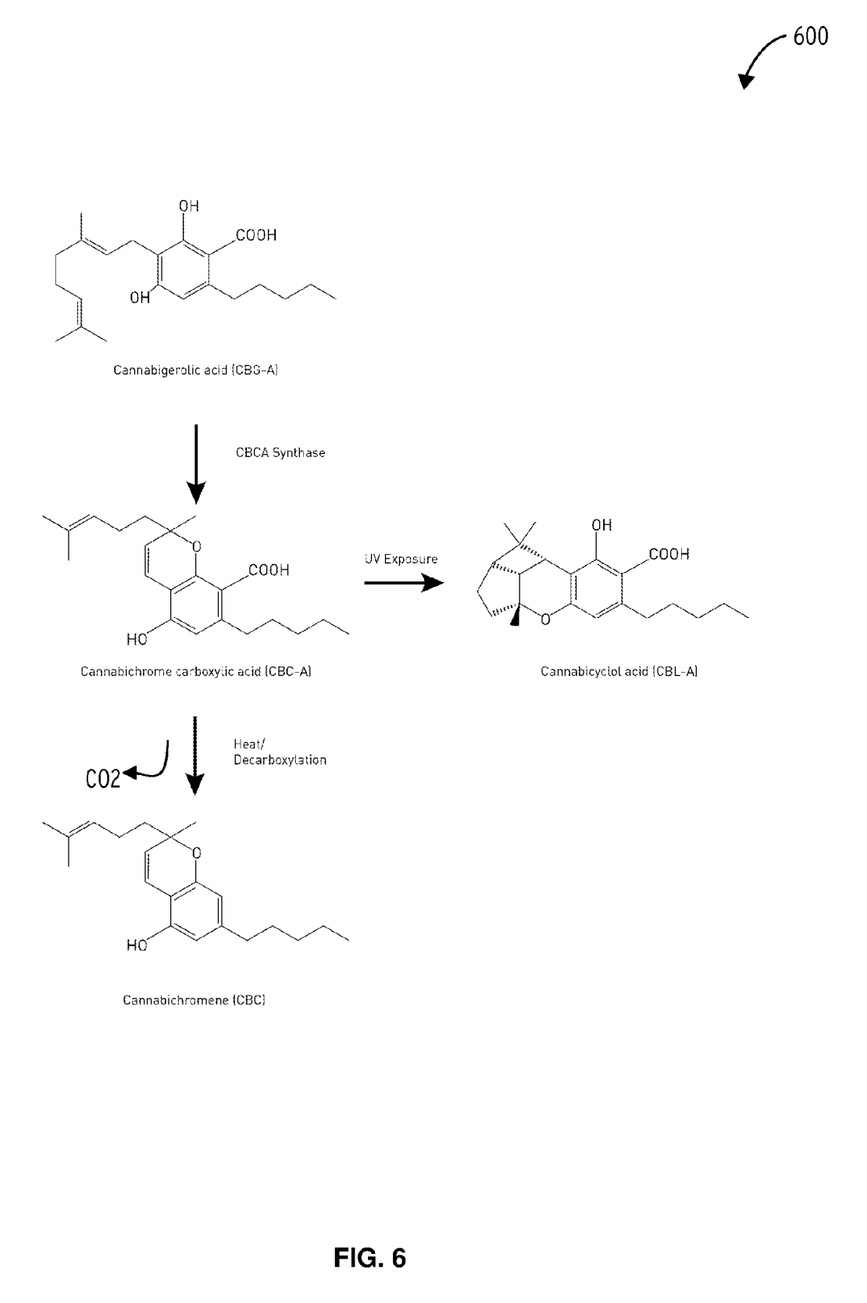
FIG. 6 illustrates biosynthesis pathway 600 showing formation of degradative products of cannabichrome carboxylic acid (CBC-A).

Referencing FIG. 6, biosynthesis pathway 600 illustrates the formation of the degradative products of cannabichrome carboxylic acid. The biosynthesis pathway 600 begins after the prenylation phase with cannabigerolic acid. Cannabichrome carboxylic acid (CBC-A) is formed following stereospecific oxidative cyclization cannabichrome carboxylic acid of by CBC-A synthase during the cyclization phase. If exposed to UV light, cannabichrome carboxylic acid may undergo UV degradation forming cannabicyclol acid a competitive product to the production of Cannabichromene (CBC). Cannabichromene is formed from cannabichrome carboxylic acid through degradative decarboxylation as a result of exposure to heat and air. The degradative decarboxylation releases $CO_2$ during the formation of the Cannabichromene.

Figure 7:
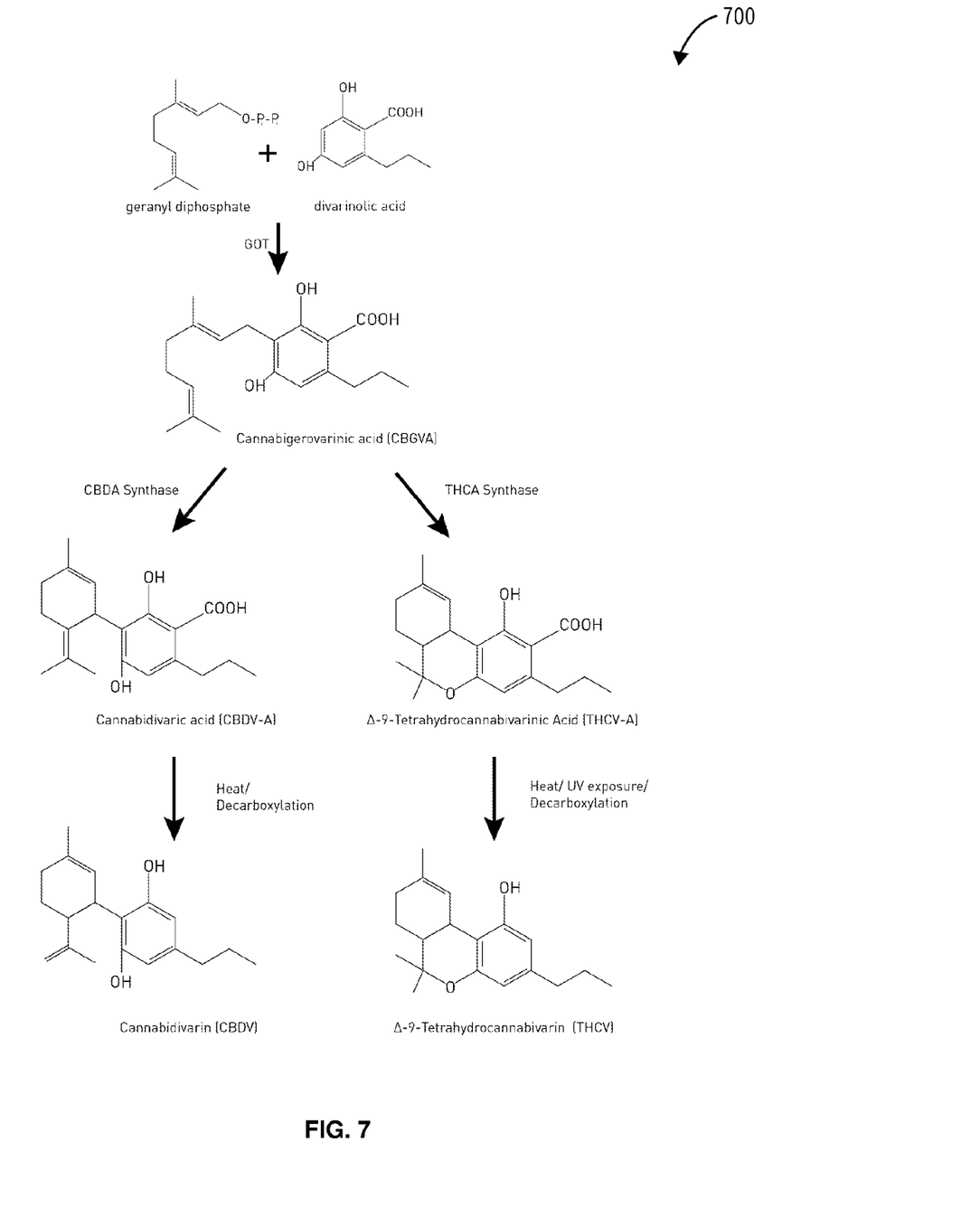
FIG. 7 illustrates biosynthesis process 700 showing the formation of Tetrahydrocannabivarin.

Referencing FIG. 7, biosynthesis process 700 illustrates the formation of Tetrahydrocannabivarin (THCV) and Cannabidivarin (CBDV) from the prenylation phase. During the prenylation phase, the geranyl diphosphate combines with an analog of olivetolic acid, divarinolic acid, which differs by having a butyl side chain instead of the pentyl side chain. The product of the prenylation phase is cannabigerovarinic acid (CBGVA), an analog of cannabigerolic acid with the same butyl replacement as divarinolic acid. CBGVA can cyclize in the same manner as cannabigerolic acid as the butyl side chain does not affect the oxidative cyclization. Cyclization of CBGVA by Cannabidiolic acid synthase produces cannabidivaric acid (CBDV-A) which is the precursor to the degradative product Cannabidivarin (CBDV) when exposed to heat and air. Similarly, cyclization of CBGVA by THCA synthase produces 9-tetrahydrocannabivarinic Acid (THCV-A) which is the precursor to the degradative product Tetrahydrocannabivarin (THCV).

Figure 8:
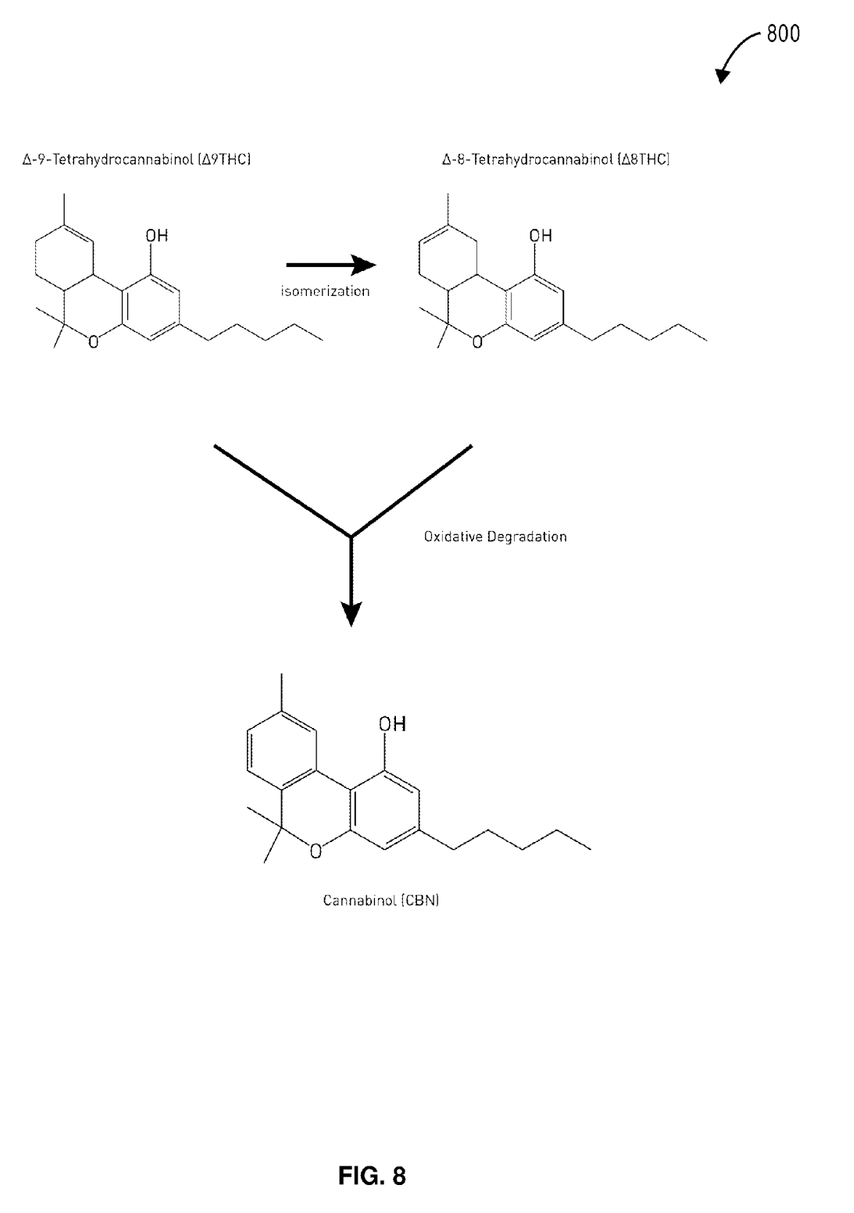
FIG. 8 illustrates degradation process 800 showing the degradation of Δ-9-tetrahydracannabinol.

Referencing FIG. 8, degradation process 800 illustrates the isomerization of Δ-9-tetrahydrocannabinol forming Δ-8-tetrahydrocannabinol. Isomerization between Δ9-THC and Δ8-THC may be attributed to photochemical properties of phytocannabinoids allowing for UV isomerization. Both isomers of THC may undergo the same oxidative degradation with prolonged exposure to UV and oxygen resulting in deprotonation and arryl ring formation.

What is claimed is:
1. A method of preserving cannabinoids in a crystalline product comprising:
   forming a slurry by combining a crystalline compound with a cannabinoid-EtOH mixture in a ratio ranging between 1:4 and 2.5:1 by weight of the cannabinoid-EtOH mixture;
   heating and agitating the slurry at a temperature ranging between 175° F. and 225° F. in a pressurized chamber between 45 and 75 minutes to form a colloidal cannabinoid-EtOH mixture;
   distributing the colloidal cannabinoid-EtOH mixture into a tray forming a mixture layer with a depth ranging between 2.0 and 4.0 inches;
   forming an evaporation vessel for the evenly distributed mixture layer through the attachment of a detachable cover to the tray;
   positioning and heating the evaporation vessel within a heating chamber to a temperature ranging between 225° F. and 300° F.;
   (i) temporarily removing the detachable cover from the tray to expose the evenly distributed mixture layer within the evaporation vessel;
   (ii) spraying pulverized dry ice on the evenly distributed mixture layer; and
   (iii) re-attaching the detachable cover to the tray;
   repeating (i)-(iii) until crystal formation is detected within the evenly distributed mixture layer; and
   removing the evaporation vessel from the heating chamber upon detection of crystal formation.

2. The method of claim 1, wherein the cannabinoid-EtOH mixture comprises 0.05 to 2.5% cannabinoids by weight of the cannabinoid-EtOH mixture, and wherein the cannabinoid-EtOH mixture is obtained from a *cannabis* extract using a filtration process.

3. The method of claim 2, wherein the cannabinoid extract comprises *cannabis* plant material combined with EtOH in a ratio of 4:1 to 8:1 (% wt) of the *cannabis* plant material to the EtOH.

4. The method of claim 2, wherein the filtration process comprises:
   heating and agitating the *cannabis* extract at a temperature ranging between 180° F. and 210° F.;
   cooling and holding the *cannabis* extract at a temperature ranging between −20° F. and 5° F. for a period of time ranging between 24 and 48 hours thereby forming a cooled suspension comprising cannabinoids and crystallized lipids in EtOH; and passing the cooled suspension through at least one membrane filter thereby separating the crystallized lipids from the cannabinoids to form the cannabinoid-EtOH mixture.

5. The method of claim 4, wherein cooling and holding the *cannabis* extract at the temperature ranging between −20° F. and 5° F. is performed to induce lipid nucleation and lipid crystal growth.

6. The method of claim 1, wherein the crystalline compound is a micronized sugar.

7. The method of claim 1, wherein the crystalline compound is a micronized sugar alcohol.

8. The method of claim 1, wherein the crystalline compound is a micronized salt.

9. The method of claim 1, wherein the crystalline product comprises cannabinoids ranging between 0.1% wt and 2.0% wt of the crystalline product.

10. A system for preserving cannabinoids in a crystalline product comprising:
- a first reactor;
- a filtration device;
- a second reactor;
- a pressurized chamber;
- an evaporation vessel comprising a detachable cover detachably coupled to a tray;
- a heating chamber;
- the first reactor being operatively disposed to receive *cannabis* plant material and ethanol;
- the first reactor being in fluid communication with the filtration device to deliver a *cannabis* extract comprising cannabinoids extracted from the *cannabis* plant material;
- the filtration device being in fluid communication with the second reactor for delivery of a cannabinoid-ethanol (EtOH) mixture separated from the *cannabis* extract;
- the second reactor being operatively disposed to receive a crystalline compound;
- the pressurized chamber being operatively disposed to receive a slurry from the second reactor;
- the tray being operatively disposed to receive a colloidal cannabinoid-EtOH mixture from the pressurized chamber forming an evenly distributed mixture layer;
- the evenly distributed mixture layer being enclosably positioned within the evaporation vessel;
- the evaporation vessel being positionable within the heating chamber;
- the evenly distributed mixture layer being in fluid communication with pulverized dry ice following detachment of the detachable cover from the tray.

11. The system of claim 10, wherein the filtration device separates crystallized lipids from the cannabinoid-EtOH mixture during filtration of the *cannabis* extract.

* * * * *